(12) United States Patent
Palmer et al.

(10) Patent No.: US 12,102,385 B2
(45) Date of Patent: Oct. 1, 2024

(54) METHOD AND SYSTEM FOR CALIBRATING A PLENOPTIC CAMERA SYSTEM

(71) Applicant: Integral Scopes Pty Ltd, Brisbane (AU)

(72) Inventors: Douglas Palmer, Brisbane (AU); Krishan Rana, Brisbane (AU); Thomas Coppin, Brisbane (AU)

(73) Assignee: INTEGRAL SCOPES PTY LTD, Red Hill Qld (AU)

( * ) Notice: Subject to any disclaimer, the term of this patent is extended or adjusted under 35 U.S.C. 154(b) by 1020 days.

(21) Appl. No.: 16/970,436

(22) PCT Filed: Feb. 19, 2019

(86) PCT No.: PCT/AU2019/050134
§ 371 (c)(1),
(2) Date: Aug. 17, 2020

(87) PCT Pub. No.: WO2019/157571
PCT Pub. Date: Aug. 22, 2019

(65) Prior Publication Data
US 2021/0118177 A1    Apr. 22, 2021

(30) Foreign Application Priority Data
Feb. 19, 2018    (AU) .................. 2018900513

(51) Int. Cl.
*A61B 3/00*    (2006.01)
*A61B 3/12*    (2006.01)
(Continued)

(52) U.S. Cl.
CPC .......... *A61B 3/0025* (2013.01); *A61B 3/0008* (2013.01); *A61B 3/12* (2013.01);
(Continued)

(58) Field of Classification Search
CPC ....... A61B 3/14; A61B 3/0025; A61B 3/0083; A61B 3/12; A61B 3/135; A61B 3/158;
(Continued)

(56) References Cited

U.S. PATENT DOCUMENTS 9,063,323 B2    6/2015  DiFrancesco
2011/0026910 A1    2/2011  Liang
(Continued)

FOREIGN PATENT DOCUMENTS

EP    3079121 A1    10/2016
EP    3162281 A1    5/2017
(Continued)

OTHER PUBLICATIONS

International Preliminary Report on Patentability for corresponding application PCT/AU2019/050134 filed Feb. 19, 2019; Mail date Sep. 26, 2019.
(Continued)

*Primary Examiner* — Brandi N Thomas
(74) *Attorney, Agent, or Firm* — CANTOR COLBURN LLP

(57) ABSTRACT

A method of calibration for a plenoptic camera system to determine the true size of an object feature in a light-field image of the object wherein the camera system comprises: an objective lens positioned along an imaging axis intersecting a point in the object; a photosensor positioned for acquiring images of portions of the object and a microlens array positioned in between the objective lens and the photosensor such that each microlens in the array projects a different view of the image formed at the image plane thereby forming an array of elemental images on the photosensor, the method comprising: acquiring an initial image of the object; extracting matching features from any plurality of views derived from a plurality of elemental images
(Continued)

forming the initial image; and calculating at least one functional relationship between two or more views having matching features.

5 Claims, 6 Drawing Sheets

(51) Int. Cl.
| | |
|---|---|
| *A61B 3/14* | (2006.01) |
| *G06T 7/80* | (2017.01) |
| *G06V 40/18* | (2022.01) |
| *H04N 23/54* | (2023.01) |
| *H04N 23/55* | (2023.01) |
| *H04N 23/56* | (2023.01) |

(52) U.S. Cl.
CPC .................. *A61B 3/14* (2013.01); *G06T 7/80* (2017.01); *G06V 40/193* (2022.01); *H04N 23/54* (2023.01); *H04N 23/55* (2023.01); *H04N 23/56* (2023.01)

(58) Field of Classification Search
CPC ....... A61B 3/102; A61B 3/1208; A61B 3/152; A61B 3/145; A61B 3/0058; A61B 3/0091; A61B 3/024; A61B 3/132; A61B 3/18; A61B 3/10; A61B 3/0041; A61B 8/10; A61B 3/0008; A61B 3/1015; A61B 3/00; A61B 3/1005; A61B 5/0095; A61B 2560/0223; A61B 3/107; A61B 3/1173; A61B 5/00; A61B 2562/0204; A61B 3/1225; A61B 5/0066; A61B 5/0077; A61B 5/01; A61B 5/1112; A61B 5/1172; A61B 5/1176; A61B 5/165; A61B 5/441; A61B 5/4836; A61B 5/7264; A61B 5/7275; A61B 18/203; A61B 2017/00203; A61B 2018/00452; A61B 2018/00589; A61B 2018/00708; A61B 2018/00714; A61B 2018/00898; A61B 2018/20359; A61B 2090/306; A61B 2090/371; A61B 2090/3735; A61B 3/028; A61B 3/09; A61B 3/13; A61B 34/35; A61B 90/37; A61B 90/90; A61B 3/0016; A61B 5/0013; A61B 5/0022; A61B 5/0075; A61B 5/1114; A61B 5/1128; A61B 5/4088; A61B 5/743; G06T 7/557; G06T 7/571; G06T 15/205; G06T 2207/10052; G06T 7/97; G06T 2200/21; G06T 7/80; G06T 2207/30041; G06T 17/00; G06T 2200/08; G06T 2210/41; A61F 2009/00846; A61F 2009/00863; A61F 9/00821; A61F 9/00825; A61F 2009/00844; A61F 2009/00851; A61F 2009/00878; A61F 2009/00897; A61F 9/00804

See application file for complete search history.

(56) References Cited

U.S. PATENT DOCUMENTS

| | | | |
|---|---|---|---|
| 2013/0127901 | A1 | 5/2013 | Georgiev |
| 2013/0329120 | A1 | 12/2013 | Hiasa |
| 2014/0146184 | A1 | 5/2014 | Meng |
| 2016/0135682 | A1 | 5/2016 | Bedard |
| 2016/0260205 | A1 | 9/2016 | Namboodiri |
| 2016/0278637 | A1* | 9/2016 | Gao .................. A61B 3/14 |
| 2017/0244957 | A1 | 8/2017 | Gao |

FOREIGN PATENT DOCUMENTS

| | | |
|---|---|---|
| EP | 3247107 A1 | 11/2017 |
| JP | 2009288042 A | 12/2009 |
| JP | 2013258449 A | 12/2013 |
| JP | 2013258453 A | 12/2013 |
| JP | 201693509 A | 5/2016 |
| JP | 2017005614 A1 | 1/2017 |
| JP | 201774377 A | 4/2017 |
| WO | 2017046397 A1 | 3/2017 |

OTHER PUBLICATIONS

International Search Report for corresponding application PCT/AU2019/050134 filed Feb. 19, 2019; Mail date May 22, 2019.
Written Opinion of the International Searching Authority for corresponding application PCT/AU2019/050134 filed Feb. 19, 2019; Mail date May 22, 2019.
European Search Report for corresponding EP19754136; Report dated Mar. 4, 2021.
Japanese Office Action for corresponding application 2020-566865; Filed Sep. 13, 2020.
Korean Office Action for corresponding application 10 2020 7027031; Mail date Apr. 22, 2023.

* cited by examiner

METHOD AND SYSTEM FOR CALIBRATING A PLENOPTIC CAMERA SYSTEM

TECHNICAL FIELD

The present invention relates to a method and system for calibrating a plenoptic camera system.

BACKGROUND

Any references to methods, apparatus or documents of the prior art are not to be taken as constituting any evidence or admission that they formed, or form part of the common general knowledge.

Integral photography was introduced by Ives and Lippmann over 100 years ago. However, integral photography has re-emerged with the introduction of the plenoptic camera. Originally presented as a technique for capturing 3D data and solving computer-vision problems the plenoptic camera was designed as a device for recording the distribution of light rays in space. One of the key advantages of plenoptic cameras is that image properties such as focus and depth of field can be adjusted after an image has been captured.

A conventional plenoptic (or light field) camera is based on an array of microlenses at the image plane of the main camera lens, with the sensor placed one focal length behind the microlenses. Usually, the array of microlenses is fixed at a small distance from a photosensor. Conventionally, the microlenses are placed and adjusted accurately to be exactly at one focal length f from the sensor, where f is the focal length of the microlenses in the array. Each microlens creates an image sampling the angular distribution of radiance at that point, which corresponds to one single direction observed from multiple points of view on the main lens aperture. Thus, the raw image captured with a conventional plenoptic camera is made up of an array of small images, typically circular, of the main lens. The conventional plenoptic camera approach swaps the placement of spatial and angular samples on the image plane: instead of producing an array of ordinary images, as in integral photography, it creates what appears as a single, recognizable "image" consisting of small 2D arrays of angular samples of a single point in the scene.

Unfortunately, due to the limitations of manufacturing processes, the exact position and orientation of the microlens array, relative to the photosensor, may vary from one camera to the next. Thus, in order to obtain accurate information from the light-field data regarding the origin of light received by the image sensor, the camera must be properly calibrated based on the actual position and orientation of the microlens array relative to the image sensor.

Certain applications of the plenoptic cameras can pose some unique challenges in calibrating the plenoptic camera.

For example, during the use of plenoptic three dimensional imaging of the retina, a prior disparity-to-depth calibration is generally required in order to reconstruct the objects' depths. Typically during calibration, a grid or point target is placed in front of the plenoptic imaging system and scanned along one axis (in case of grid target) or three spatial axes (in case of point target). However, when imaging the eye, such a procedure cannot be used because the eye's crystalline lens is also a part of the imaging system and it is simply not possible to put a target with "known" depth inside the individual's eye. Additionally, the accommodative power, tangential and axial misalignments of the eye are constantly changing and so the actual nature of the retinal imaging instrument is different for every shot.

Currently available retinal imaging instruments such as digital fundus cameras or OCT units are often large, desk mounted units with significant system complexity and cost devoted to the problem of maintaining reliable imaging conditions, particularly the correct distance of the camera optics to the patient's eyeball and stable eye fixation to properly align the patient's line of sight to that of the camera. If either of these conditions are not met, the resulting image can be out of focus, obscured by flash light glare or exhibit other optical artefacts that reduce the fidelity of the image or obscure significant retinal details.

The correct and accurate measurement of retinal features from retinal topography is crucial in diagnosing and monitoring of Age-Related Macular Degeneration (AMD), Glaucoma, Diabetic Retinopathy and Macula Oedema. In view of the above, there is a need to provide an improved method of calibrating retinal plenoptic cameras for at least addressing some of the problems of the prior art.

SUMMARY OF INVENTION

In one aspect, the invention provides a method of calibration for a plenoptic camera system to determine the true size of an object feature in a light-field image of the object wherein the camera system comprises: an objective lens positioned along an imaging axis intersecting a point in the object; a photosensor positioned for acquiring images of portions of the object and a microlens array positioned in between the objective lens and the photosensor such that each microlens in the array projects a different view of the image formed at the image plane thereby forming an array of elemental images on the photosensor; the method comprising:

acquiring an initial image of the object;

extracting matching features from any plurality of views derived from a plurality of elemental images forming the initial image; and calculating at least one functional relationship between two or more views having matching features.

In another aspect, the invention provides a method of calibration for an ophthalmic plenoptic camera system to determine a true size of a feature of the retina of a subject's eye based on an acquired light-field image or light-field images of the retina, wherein the imager comprises: an illumination light source and an optical assembly for directing light from the light source into an eye of a subject; an objective lens positioned along an imaging axis intersecting a point on the fundus of the eye; a photosensor positioned for acquiring images of portions of a fundus of the eye and a microlens array positioned in between the objective lens and the photosensor such that each microlens in the array projects a different view of the image formed at the image plane thereby forming an array of elemental images on the photosensor; the method comprising:

acquiring an initial image of the retina;

extracting matching features from views derived from a plurality of elemental images forming the initial image;

calculating at least one functional relationship between two or more views having matching features.

In an embodiment, the calculating step comprises calculating at least two functional relationships between two or more said views having matching features.

In an embodiment, the step of applying the functional relationship to calculate the intrinsic parameters a virtual camera wherein the imaging system comprises a plurality of said virtual cameras.

In an embodiment, the method further comprises the step of applying the functional relationship to calculate the true size of an object feature in the object. Similarly, the method may also comprise the step of applying the functional relationship to calculate the true size of a feature in the retina of the subject's eye.

In an embodiment, the method in accordance with anyone of the preceding claims wherein the step of extracting matching features comprises applying a feature detecting step by identifying groups of two or more points that are easily distinguishable in the two or more views to produce a set of matching pairs.

In an embodiment, the step of producing matching pairs is followed by a co-matching step between the matching pairs across the corresponding views to obtain co-matches between match pairs and subsequently appending the co-matches together to obtain a cluster of matching points across the corresponding views.

In yet another aspect, the invention provides a system comprising:
one or more processors; and
a non-volatile memory comprising instructions executable by said one or more processors to perform a method of calibration for a plenoptic camera system to determine the true size of an object feature in a light-field image of the object wherein the camera system comprises: an objective lens positioned along an imaging axis intersecting a point in the object; a photosensor positioned for acquiring images of portions of the object and a microlens array positioned in between the objective lens and the photosensor such that each microlens in the array projects a different view of the image formed at the image plane thereby forming an array of elemental images on the photosensor; the method comprising:
acquiring an initial image of the object;
extracting matching features from any plurality of views derived from a plurality of elemental images forming the initial image; and
calculating at least one functional relationship between two or more said views having matching features.

In another aspect, the invention provides a system comprising
one or more processors; and
a non-volatile memory comprising instructions executable by said one or more processors to perform a method of calibration for an ophthalmic plenoptic camera system to determine a true size of a feature of the retina of a subject's eye based on an acquired light-field image or light-field images of the retina, wherein the imager comprises: an illumination light source and an optical assembly for directing light from the light source into an eye of a subject; an objective lens positioned along an imaging axis intersecting a point on the fundus of the eye; a photosensor positioned for acquiring images of portions of a fundus of the eye and a microlens array positioned in between the objective lens and the photosensor such that each microlens in the array projects a different view of the image formed at the image plane thereby forming an array of elemental images on the photosensor; the method comprising:
acquiring an initial image of the retina;
extracting matching features from views derived from a plurality of elemental images forming the initial image;
calculating a functional relationship (F) between two or more said views having matching features.

DETAILED DESCRIPTION

Figure 1:
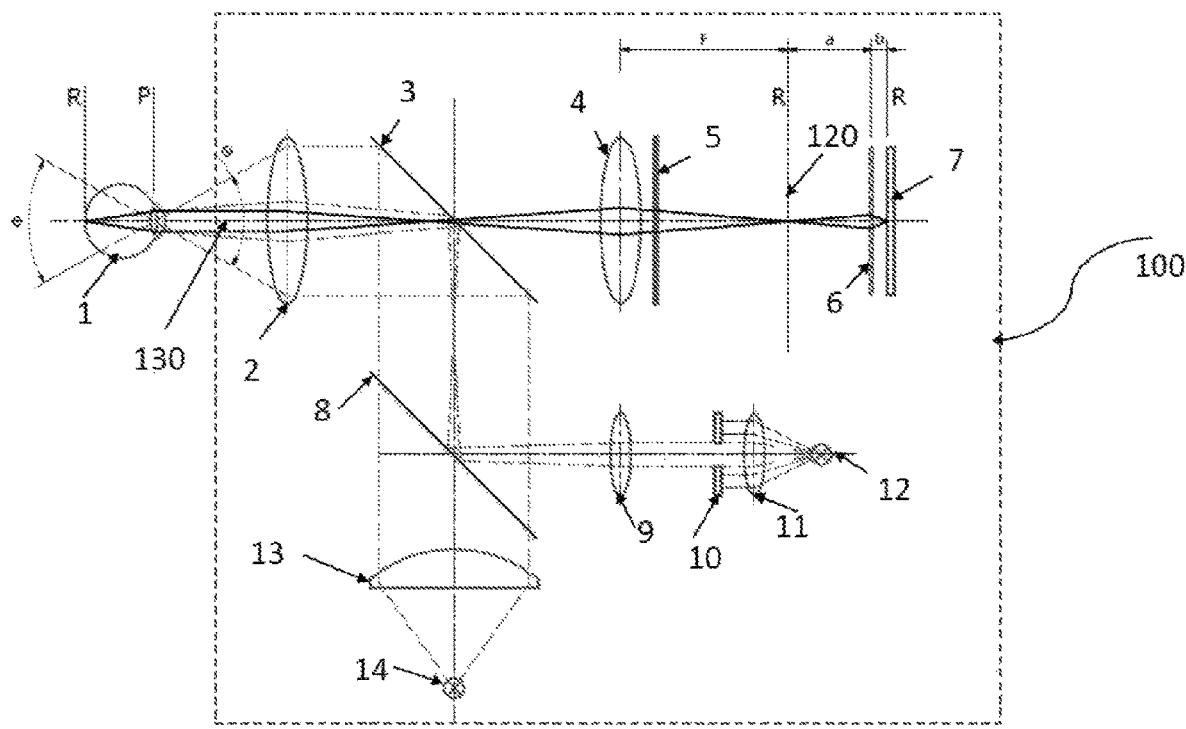
FIG. 1 is a schematic illustration of an ophthalmic imaging apparatus 100 for use in conjunction with a method and system embodiment of the present invention.

Referring to FIG. 1, a schematic diagram of an ophthalmic plenoptic camera system 100 is illustrated. The ophthalmic camera system (100) is provided for capturing a plurality of images of the fundus of a subject's eye 1 in a single view. The term "fundus" refers to a posterior pole of the eyeball and generally comprises the retina (which includes the macula and the optic nerve).

A typical fundus image acquisition method involving the use of the apparatus 100 involves guiding the eye (1) to the correct axial alignment by the use of a fixation assembly that comprises a fixation target (10) whose image is formed at the retinal plane (R). The fixation target is rear illuminated by a low power LED (12) collimated by a lens (11) and its image focused by lens (9) through a plate beam splitter (8) to a plane, one focal length to the rear of the objective lens (2). This is then projected by the objective lens (2) and as a result, the fixation target (10) is imaged by the eye. To the eye, the fixation target (10) appears at an infinite distance. As a result, the fixation target (10) remains in focus for a relaxed emmetropic eye.

Light for retinal illumination of the eye (1) is provided by an LED source (14) which is focused by a condenser lens (13) into a collimated beam. This light from the LED source (14) is then directed into the main optical path of the ophthalmic apparatus 100 via a plate beam splitter (3) and through the objective lens (2). The beam directed by the beam splitter (3) is then focused at or slightly behind the pupil plane of the eye (P) and fans out within the eye to illuminate the retinal surface radially. The illumination LED has a 'warm white' radiance of 2700K. This spectrum has a reduced output in the blue range (<450 nm) which is most responsible for the photochemical mechanism of eye damage. The radiant power of the illumination at the pupil plane is significantly reduced compared to that delivered by the LED due to losses in the system, primarily the low reflectance ratio of the beam splitters, and is designed to ensure the safety of the patient as well as maximising signal to noise ratio of the image.

The ophthalmic plenoptic camera system (100) comprises a photosensor array (7) positioned for acquiring images of portions of the fundus of the eye (1). The objective lens (2) is positioned along an imaging axis (130) which intersects a point on the fundus of the eye (1). The objective lens (2) is positioned for refracting light that has been reflected by the fundus to form an image of the fundus on an image plane (120) of the objective lens (2). Light reflected from the retina of the emmetropic eye (1) is collimated by the optical elements of the human eye (1) and emitted through the iris of the eye (1). This radiance of the light emitted out of the eye (1) is captured over a wide angle by the objective lens (2) and is focused to a plane, specifically an image plane where the image is inverted and relayed via a positive relay lens (4) to a microlens array (6). Signal to noise ratio is improved by filtering excessive objective backscatter using a single linear polarization filter (5). The image plane is positioned away from the photosensor array (7) and the microlens array (comprising a plurality of microlenses) is positioned in between the objective lens (2) and the photosensor array (7) such that each microlens in the array is adapted for projecting at least a portion of the image formed on the image plane of the relay lens (4) onto the photosensor array (7).

In at least some embodiments of the ophthalmic imaging apparatus 100, the microlenses of the microlens array (6) are focused on an image of the fundus formed by the relay lens (4), instead of being focused on the relay lens (2), as in conventional plenoptic cameras. The arrangement of the microlens array (6) in the aforementioned configuration of the present ophthalmic imaging apparatus (100) helps in achieving sharper and higher spatial resolution images. The objective lens (2) in combination with the relay lens (4) forms a real image of the fundus in the image plane. The image plane is simply a location in space that can be considered to have an image "in the air" as created by the objective lens (2) and the relay lens (4). The microlenses of the microlens array (6) being focused on the image plane capture the image of the fundus formed at the image plane. Each microlens captures a small area or region of the image at the image plane and maps or projects the captured region onto a corresponding region of the photosensor array (7).

Figure 2:
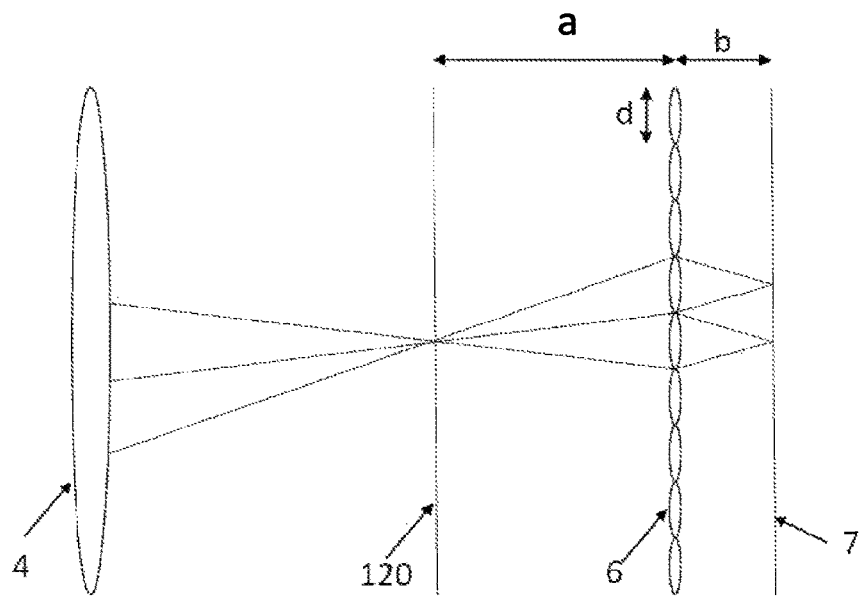
FIG. 2 is an enlarged schematic view of the microlens array (6) and the photosensor array (7) which form a part of the ophthalmic imaging apparatus 100.

During use, the microlens array (6) samples u×v elemental images at a spatial resolution equivalent to the sensor size in pixels multiplied by the ratio of b/a as shown in FIG. 2. The microlens array (6) may consist of either square microlens elements arranged in an orthogonal pattern or close packed hexagonal elements. The distances b and a are typically larger than the focal length of the microlenses but may be smaller in which case the microlens array samples the virtual image formed by the relay lens (4).

The elemental images are formed on the photosensor array (7) which may be of any known type such as a charge coupled device (CCD) type or complementary metal-oxide-semiconductor (CMOS). For colour imaging, the image sensor will typically feature a Colour Filter Array to allow separation of RGB colour channels via a demosaicing process but alternative sensor technologies such as Foveon 3X may also be utilised. A monochromatic sensor may also be used in conjunction with visible or infrared illumination or by using burst photography with separate colour channels recorded in quick succession under different wavelength illumination. The resultant radiance captured by the photosensor array (7) in an image therefore consists of a multitude (u×v) of elemental images of size s×t pixels.

It is important to note that each elemental image (300) captured by the photosensor array (7) as a result of an individual microlens in the microlens array (6) provides a slightly different perspective view of the fundus of the eye. In other words, each elemental image incident on a predetermined number of pixels of the photosensor array (7) is representative of light passing through an individual microlens in the microlens array (6). By focusing the microlenses of the microlens array (6) on the image produced by the relay lens (4), embodiments of the present ophthalmic system (100) are able to better capture the positional information of the light-field. A light field rendering method may also be used to render images from light fields captured by photosensor array (7) at a higher spatial resolution than conventional light field rendering techniques.

The imaging process or method 500 of the presently described ophthalmic imaging system (100) may be understood to be comprised of three main steps that include: (A) acquiring an initial image of the retina; (B) extracting matching features from views derived from a plurality of elemental images forming the initial image; and (C) calculating at least one functional relationship between two or more perspective views having matching features as will be explained in further detail in the foregoing sections.

The general method (500) may be employed for calibrating the ophthalmic plenoptic camera system in two distinct configurations.

Figure 3:
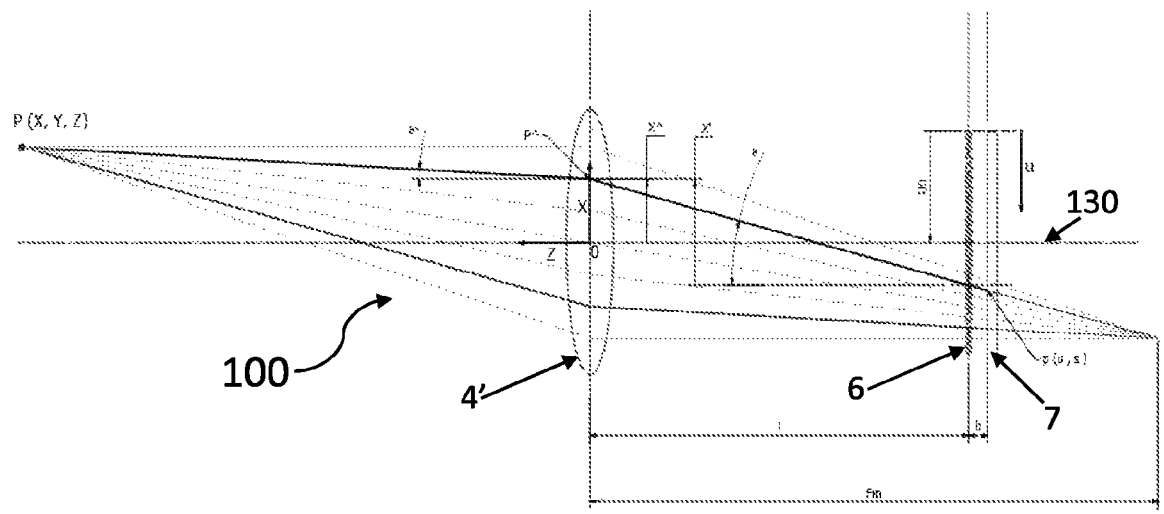
FIG. 3 is a detailed schematic view of the microlens array (6) and the photosensor array (7) which form a part of the ophthalmic imaging apparatus 100.
Figure 4:
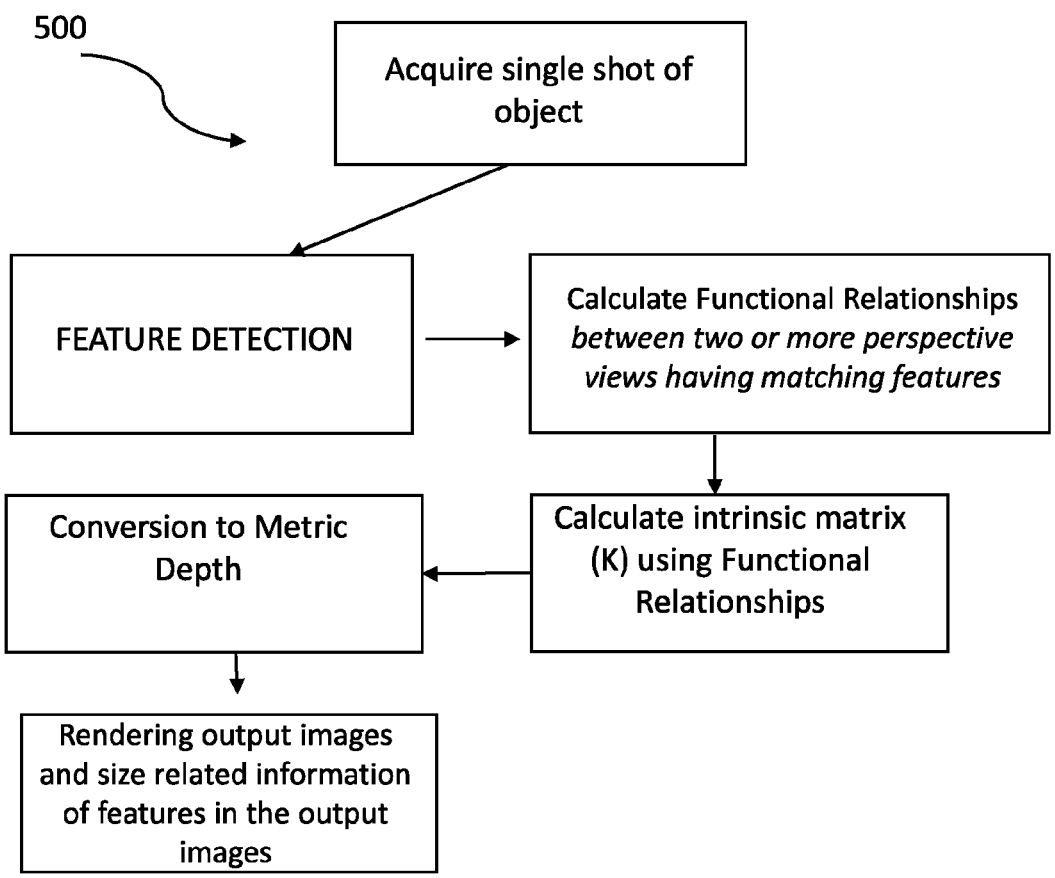
FIG. 4 is a flow chart for a method 500 in accordance with an embodiment.

A first method (500A) is directed for use in determining a camera model that relates the point P(X,Y,Z) with its positions on the sensor 7 for the system 100 shown in FIG. 3. This method relies on approximating the microlens array 6 as a series of pinholes, and all of the other optics as a single thin lens 4. A discrete point p(u,v,s,t) on the sensor 7 (s & t are the pixel's position under the microlens indexed from 1, and u & v are the microlens the ray passes through, indexed from 1) can then be reprojected through the camera to its point in space P(X,Y,Z). Note that for the presently described embodiment, the distance between the sensor 7 and the microlens array 6 is b, the distance between the main lens and the microlens array is l and the focal length of the main lens is $f_m$. This will be referred to as the "Plenoptic 2 configuration" throughout the specification.

Figure 5:
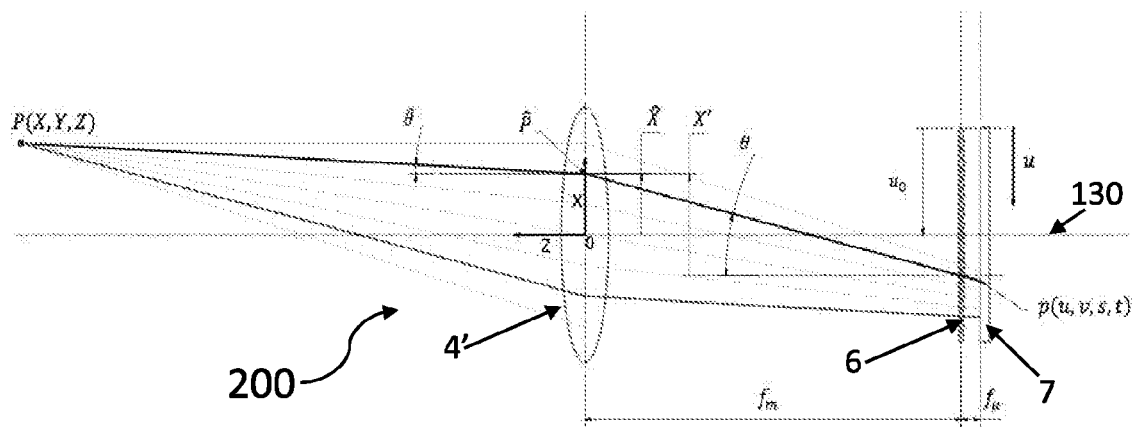
FIG. 5 is a detailed schematic view of the microlens array (6) and the photosensor array (7) which form a part of another ophthalmic imaging apparatus 200.

A second method (500B) is directed for use in determining a camera model that relates the point P(X,Y,Z) with its positions on the sensor 7 for the system 200 shown in FIG. 5. The arrangement shown in FIG. 5 requires the image plane to be positioned at the photosensor array (7) and the microlens array (6) (comprising a plurality of microlenses) is positioned in at the focal length $f_m$ of the objective lens (2). The photosensor array (7) is positioned relative to the microlens array (6) such each microlens in the array is adapted for projecting at least a portion of the image formed on the microlens array (6) onto the photosensor array (7). The only difference in between the system 200 and the previously described apparatus 100 is that l=$f_m$ and b=$f_\mu$, where $f_\mu$ is the focal length of the microlens and $f_m$ is the focal length of the lens (4). The system (200) will be referred to as the "Plenoptic 1 configuration".

A plenoptic camera splits incoming ray bundles from object space at the aperture of the camera using a microlens array. This results in a multitude of elemental images being formed on the sensor. Each pixel in these elemental images can be said to be representative of a discrete set of rays emanating from the object point.

Figure 6A:
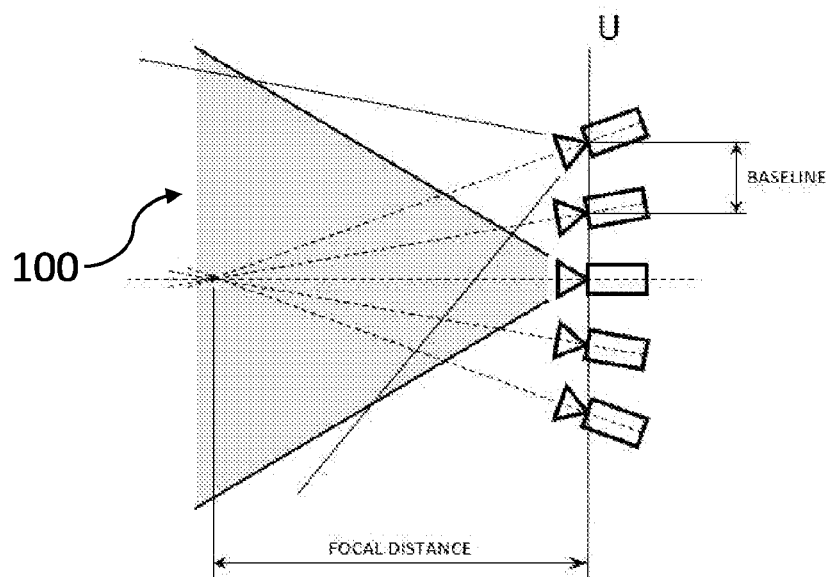
FIGS. 6A and 6B illustrate arrangement of virtual camera arrays for the plenoptic 2 configuration (FIG. 6A) and for the plenoptic 1 configuration (FIG. 6B).
Figure 6B:
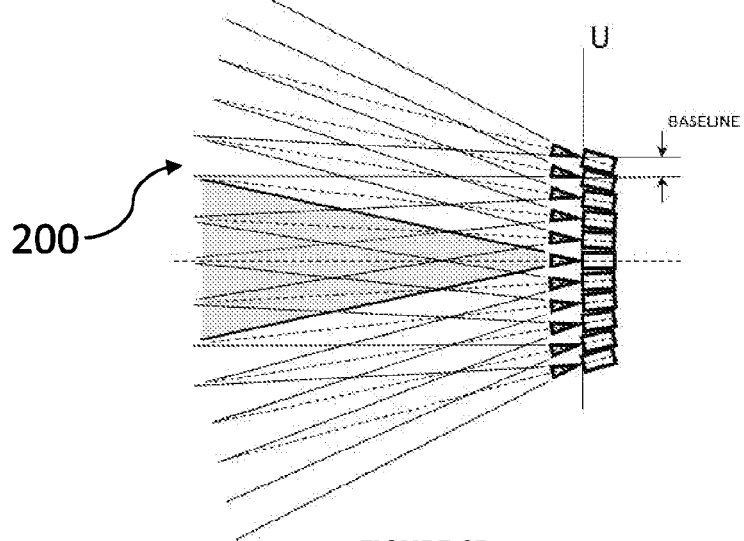

For the purpose of creating perspective views, it is useful to abstract this ray space representation to that of an array of simple pinhole perspective cameras, each one at a different position. FIGS. 6A and 6B show the two variants of microlens based plenoptic cameras as equivalent camera arrays for the plenoptic 2 and the plenoptic 1 systems respectively.

The Penoptic 1 configuration as shown in FIG. 6B, virtual cameras have mostly overlapping fields of view (FOV) and show vergence towards the intersection of focal plane and optical axis of real camera. The number of virtual cameras in the array is equal to the number of pixels under each microlens. The FOV of each camera is approximately equal to that of the entire camera array and the image resolution is equal to the number of microlenses in the array.

For the Plenoptic 2 configuration plenoptic cameras as shown in FIG. 6A, the virtual cameras have partially overlapping fields, diverging away from the optical axis of the real camera. The FOV of each camera is equal to that of each microlens and the resolution equal to the number of pixels behind each microlens, ie. the elemental image size. The number of virtual cameras is equal to the number of microlenss in the array and the overall field of view is the sum of these individual fields divided by the multiplexing ratio.

Feature Detection

Feature detection is applied to the light field to identify groups of two or more points in image space that correspond to the same point in object space. Feature detection involves finding areas within an image that are easily distinguishable from other areas (at least in the eyes of a computer) and then creating a descriptor for the area that encodes what is unique about that specific portion of the image. The point in the image and the descriptor that encodes what it looks like are then referred to as the feature.

Feature matching involves performing feature detection on at least two images, and then searching for features in the two images that have similar descriptors. A distance metric is used to compare two descriptors and a match is made when this value is lower than a chosen threshold. In the case of multiple images, clustering is used to combine sets of matching pairs to obtain a complete set of matching points.

Figure 7:
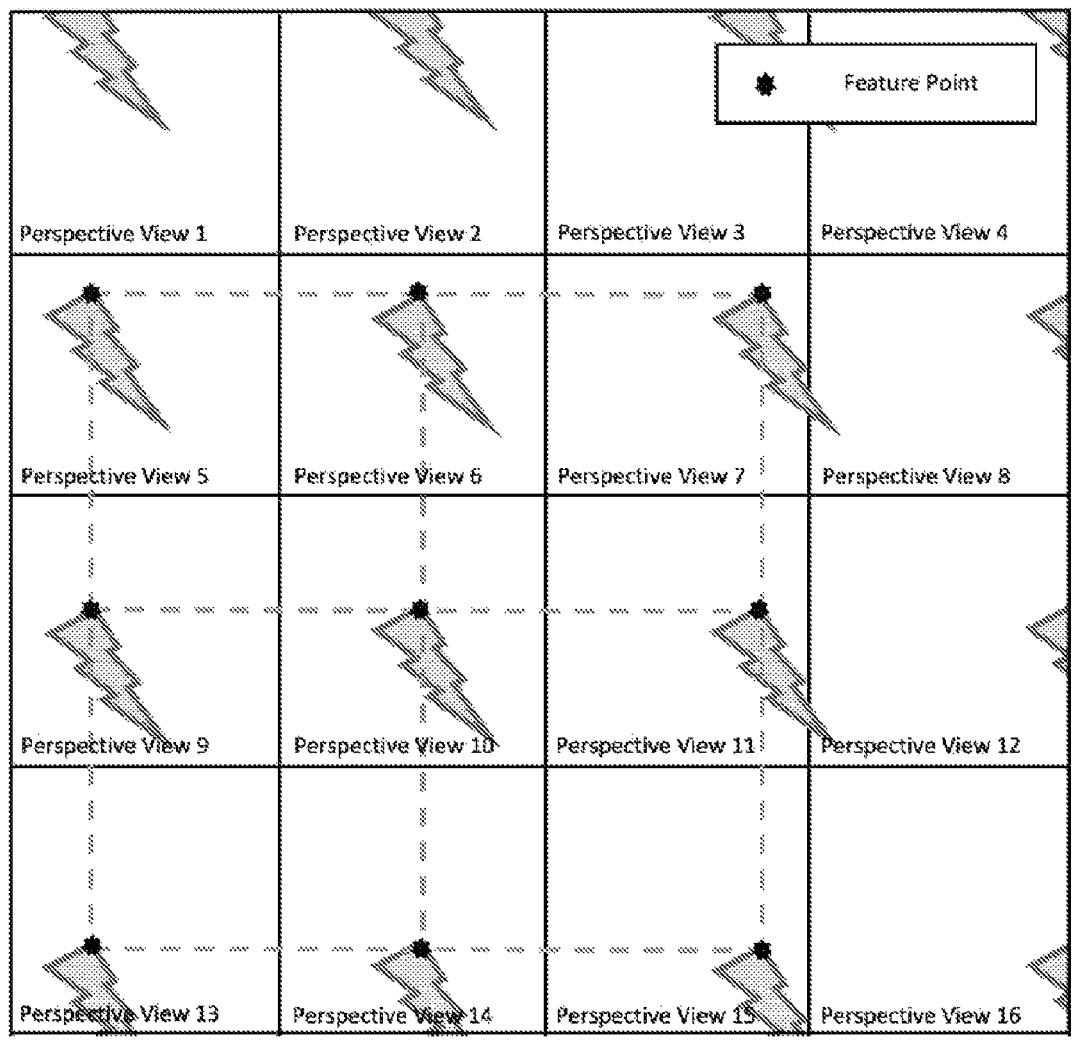
FIG. 7 illustrates the feature matching step for a plenoptic 2 camera.

To apply feature detection and matching on light field imagery, feature detection must be performed between adjacent perspective views to produce a set of matching pairs. Co-matches between match pairs may then be appended together to obtain a cluster of matching points across the corresponding perspective views. This is illustrated in FIG. 7 for a plenoptic 2 system. To filter out unreliable clusters, the coefficient of determination ($R^2$), which explains how well the data fits to a line, is computed for each line formed by the coordinates (t,v) and (s,u) from a given cluster. A threshold is chosen to reject or accept the cluster based on these $R^2$ values. Accounting for distortion, the set of points (t,v) and (s,u) should sit close to a linear fit and significant deviation from this trend indicate incorrect matches and hence an unreliable cluster.

A pair (or more) of images that view the same point in object space is needed to perform feature matching, and these images may be created by deriving a set of perspective views from the array of elemental images that makes up the light field. The method for deriving perspective views is different for the Plenoptic 1 and Plenoptic 2 systems and an overview of both approaches is provided below. The perspective views generated using these methods will correspond to the set of images captured by the virtual camera arrays described above.

A point in the perspective view is represented as (i,j,x,y), where (i,j) is the index of the perspective view the point belongs to, and (x,y) is the location of the point within this perspective view.

Figure 8:
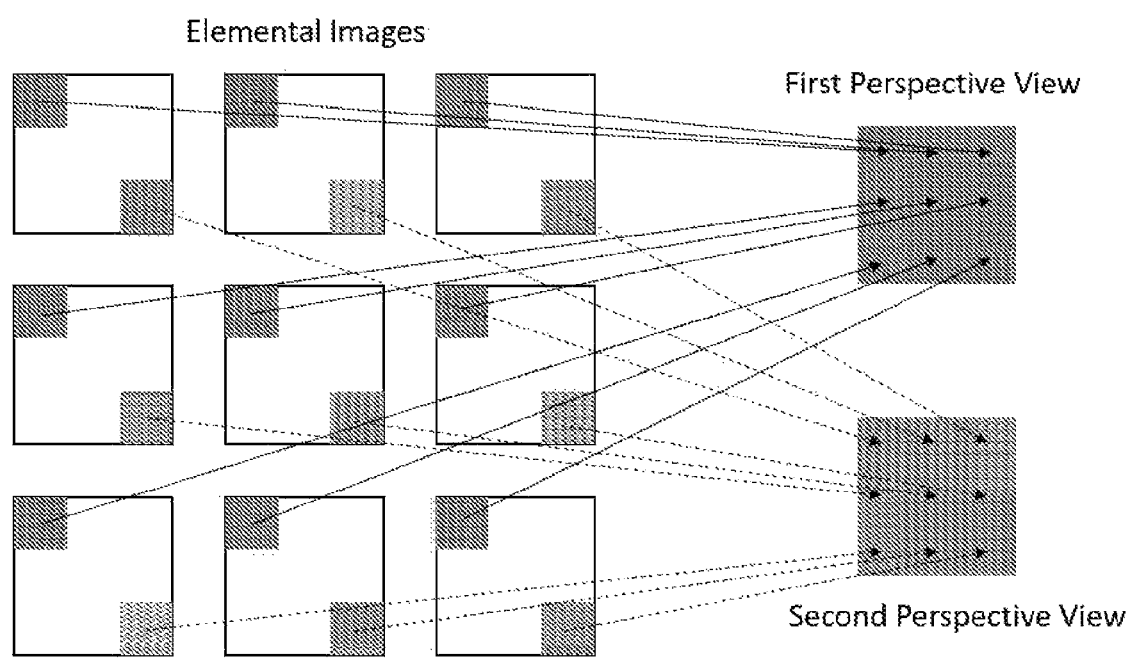
FIG. 8 illustrates the step of generating perspective views from plenoptic 1 lightfields.

Generating perspective views from plenoptic 1 light fields involves taking one pixel from each elemental image and then tiling them together, noting that the location of the pixel within each elemental image must be the same. For example, that we can generate a first perspective view by taking the top-left pixel from each elemental image, and then a second perspective view by taking the bottom-left pixel from each elemental image. This process is illustrated in FIG. 8.

Generating a set of perspective views from a plenoptic 2 light field is theoretically simpler as each elemental image is a perspective view as shown in FIG. 7. However this is complicated by the fact that the elemental images are small, and as such have only a small shared field of view which limits the number of potential matches between pairs of images.

Calculating the Functional Relationships (F) Between Two or More Perspective Views Having Matching Features Once the location of matching points in two (or more) views is known from feature matching, then the next step for the calibration method is to calculate the functional relationship between the matching points.

In the presently described embodiment, a fundamental matrix [F] between the pair of corresponding points is calculated. The fundamental matrix encodes a geometric constraint that can be estimated between the two images, which is known in the art as the epipolar (geometry) constraint. In particular, the epipolar geometry represents the fact that a given point in a given scene and the two optical centers of two given images of the scene lie on the same (epipolar) plane. This means that a given a point in one of the images, its corresponding point in the other image must lie on a known (epipolar) line.

The fundamental matrix F defines a relationship between the location of points in one image x, and the corresponding locations of the points in a second image x'.

$$x'^T F x = 0.$$

for any pair of matching points x↔x' in two images. Given sufficiently many point matches $x_i \leftrightarrow x'_i$ (at least 8), the above equation can be used to compute the unknown matrix F. In particular, writing $x=(x, y, 1)^T$ and $x'=(x', y', 1)^T$ each point match gives rise to one linear equation in the unknown entries of F. The coefficients of this equation are easily written in terms of the known coordinates x and x'. Specifically, the equation corresponding to a pair of points (x, y, 1) and (x, y', 1) is $$x'xf_{11}+x'yf_{12}+x'f_{13}+y'xf_{21}+y'yf_{22}+y'f_{23}+xf_{31}+yf_{32}+f_{33}=0,$$

Let f be the 9-vector made up of the entries of F in row-major order. Then the above equation can be expressed as:

$$(x'x,x'y,x',y'x,y'y,y',x,y,1)f=0.$$

From a set of n point matches, a set of linear equations of the form as shown below can be obtained $$Af = \begin{bmatrix} x'_1 x_1 & x'_1 y_1 & x'_1 & y'_1 x_1 & y'_1 y_1 & y'_1 & x_1 & y_1 & 1 \\ \vdots & \vdots & \vdots & \vdots & \vdots & \vdots & \vdots & \vdots & \vdots \\ x'_n x_n & x'_n y_n & x'_n & y'_n x_n & y'_n y_n & y'_n & x_n & y_n & 1 \end{bmatrix} f = 0.$$

F is a singular matrix of rank 2, and so has 8 free parameters, which means a minimum of 8 matching points is needed to determine the fundamental matrix.

The first view can be chosen as the canonical camera so that $P^1=[I|0]$ then the camera matrix (which is a way to represent how a second camera is positioned with respect to another camera) for any other view may be calculated as:

$$P^i=[[e^{\prime i}]\times F^i | e^{\prime i}],$$

where $F^i$ is the fundamental matrix between the 1st and i-th view, and $e^{\prime i}$ is the epipole of the i-th view, which can be calculated as the left null-space of $F^i$.

The intrinsic matrix for a virtual camera (this relationship is based on the assumption that the plenoptic system is comprised of a plurality of such virtual cameras that are identical as previously described) is defined as:

$$K = \begin{bmatrix} f & 0 & x_0 \\ 0 & f & y_0 \\ 0 & 0 & 1 \end{bmatrix}$$

where f is the focal length of the virtual camera, and $(x_0; y_0)$ is the principal point. The dual image of the absolute conic for a camera with intrinsic matrix K is given by $w^*=KK^T$. It is also known that for a given virtual camera matrix P, the absolute dual quadric $Q^*_\infty$ is projected as the dual image of the absolute conic, $$K^i K^{iT} = w^{*i} = P^i Q^*_\infty P^{iT}$$

The above equation forms the basis of (one of the forms of) auto-calibration, where constraints on the values of K allow for the determination of $Q^*_\infty$ which in turn allows for the calculation of K, thus calibrating the camera.

As a way to explain this step more clearly, basically the absolute dual quadric is related to the plane at infinity in a purely Euclidean space (ie no projection or cameras or anything else), then it would be defined by diag(1,1,1,0). Imaging it using a camera then applies a homography to the quadric, making it look like $H Q^*_\infty H^T$. However, during imaging, a 3D space is turned into a 2D image, and the 2D image of a 3D quadric is a conic. It is important to note that the quadric is the same for any camera that exists in the same space, which is why it is independent of i in the equation and is what allows the problem to be solved. The other important thing to note is the dual image of the absolute conic is dependent on the camera intrinsic matrix, which means if all the cameras are identical, then so are all of the $w^{*i}$'s.

$Q^*_\infty$ is a symmetric 4×4 matrix which means it has 10 independent elements, and so 10 independent equations are needed to determine it. By assuming all of the virtual cameras are identical (a safe assumption for a plenoptic camera), and noting that the homogeneity of the quantities leaves them equal only up to scale, the relation above will generate a set of 5 quadratic equations for each perspective view pair as a result of which at least two functional relationships would need to be calculated to get the required 10 equations:

$$w_{11}^{*i}/w_{11}^{*j}=w_{12}^{*i}/w_{12}^{*j}=w_{13}^{*i}/w_{13}^{*j}=w_{22}^{*i}/w_{22}^{*j}=w_{23}^{*i}/w_{23}^{*j}=w_{33}^{*i}/w_{33}^{*j}$$

Given a minimum of 3 views, the ten equations can be solved to find $Q^*_\infty$, which can in turn allow for the calculation of K, the calculation of the baseline between view pairs and the conversion of the projective space to a metric space.

Note that certain configurations of cameras are degenerate cases and result in a fewer number of independent equations per view pair, and in these cases, more view pairs will be required. This will not be an issue for the plenoptic camera as we have more than enough view pairs.

Conversion to Metric Depth

The conversion to metric space is relatively straightforward if the intrinsic matrix (K) of the cameras that make up the virtual camera array, and the baseline (B) between view pairs is known. The position of a point in object space (X,Y,Z) can either be calculated using triangulation or by using:

$$X = \frac{B(x-x_0)}{k}, Y = \frac{B(y-y_0)}{k}, Z = \frac{fB}{\rho k}$$

where f is the focal length of the camera, $(x_0, y_0)$ is the principal point of the virtual camera (x,y) is the coordinate of the point, p is the size of a pixel (from sensor datasheet), k is the disparity of the point (i.e. how much the point moves from one view to the next) and B is the baseline between the two cameras. B may be calculated from knowledge of the intrinsic parameters by either; estimation of virtual camera poses, estimation of ray intersection using camera transfer matrices or through knowledge of camera optics (location and size of entrance pupil).

Figure 9:
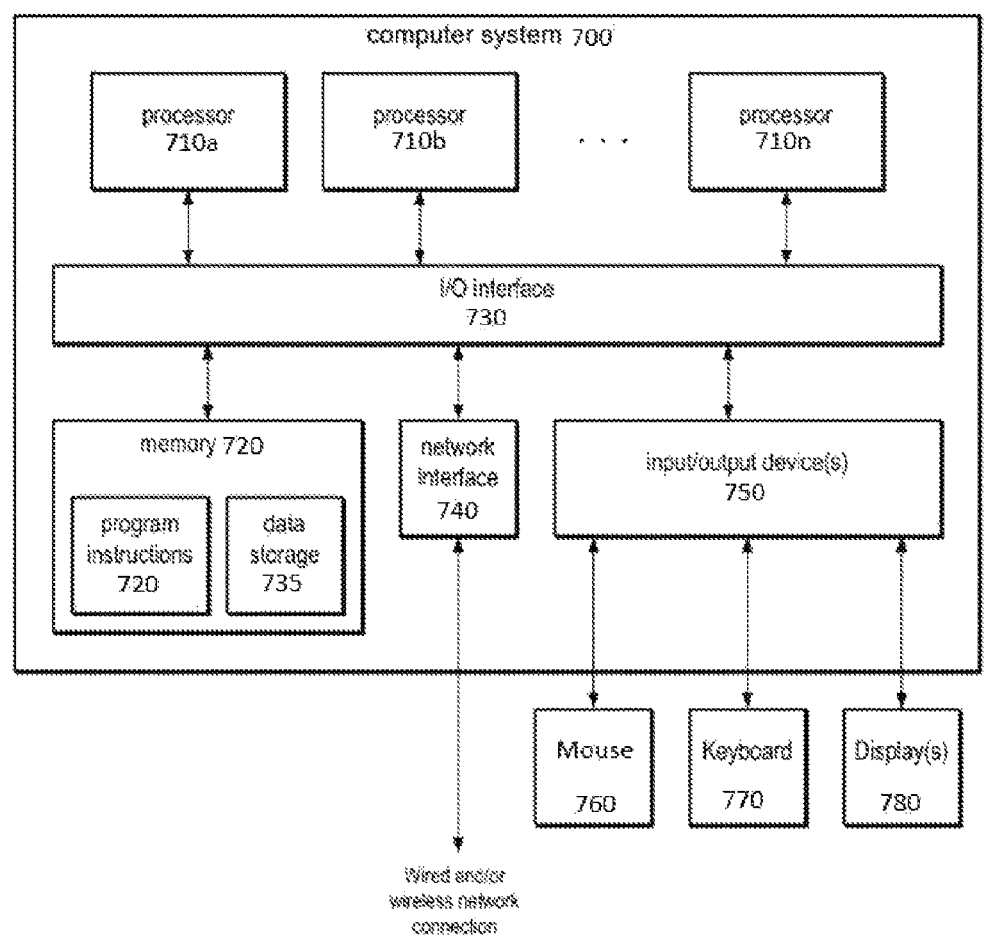
FIG. 9 illustrates an example computer system that may be used in conjunction with apparatus 100 or 200 for executing method 500.

Referring to FIG. 9, an example system for calibrating or rendering output retina images has been illustrated.

Embodiments of a one or more of the various calibration or image rendering methods as described herein may be executed on one or more computer systems, which may interact with various other devices. One such computer system is illustrated by FIG. 5. In different embodiments, computer system 700 may be any of various types of devices, including, but not limited to, a personal computer system, desktop computer, laptop, notebook, or netbook computer, mainframe computer system, handheld computer, workstation, network computer, a camera, a set top box, a mobile device, a consumer device or in general any type of computing or electronic device.

In the illustrated embodiment, computer system 700 includes one or more processors 710 coupled to a system memory 720 via an input/output (I/O) interface 730. Computer system 700 further includes a network interface 740 coupled to I/O interface 730, and one or more input/output devices 750, such as a mouse device 760, keyboard 770, and display(s) 780. In some embodiments, it is contemplated that embodiments may be implemented using a single instance of computer system 700, while in other embodiments multiple such systems, or multiple nodes making up computer system 700, may be configured to host different portions or instances of embodiments.

In some embodiments, at least one processor 710 may be a graphics processing unit. A graphics processing unit or GPU may be considered a dedicated graphics-rendering device for a personal computer, workstation or other computing or electronic device. Modern GPUs may be very efficient at manipulating and displaying computer graphics, and their highly parallel structure may make them more effective than typical CPUs for a range of complex graphical algorithms. The GPU(s) may implement one or more application programmer interfaces (APIs) that permit programmers to invoke the functionality of the GPU(s). Suitable GPUs may be commercially available from vendors such as NVIDIA Corporation, ATI Technologies, and others.

System memory 720 may be configured to store program instructions and/or data accessible by processor 1010. In various embodiments, system memory 720 may be implemented using any suitable memory technology, such as static random access memory (SRAM), synchronous dynamic RAM (SDRAM), non-volatile/Flash-type memory, or any other type of memory. In the illustrated embodiment, program instructions and data implementing desired functions, such as those described above for embodiments of a calibration module are shown stored within system memory 1020 as program instructions 725 and data storage 735, respectively. In other embodiments, program instructions and/or data may be received, sent or stored upon different types of computer-accessible media or on similar media separate from system memory 720 or computer system 7000. Generally speaking, a computer-accessible medium may include storage media or memory media such as magnetic or optical media, e.g., disk or CD/DVD-ROM coupled to computer system 7000 via I/O interface 730. Program instructions and data stored via a computer-accessible medium may be transmitted by transmission media or signals such as electrical, electromagnetic, or digital signals, which may be conveyed via a communication medium such as a network and/or a wireless link, such as may be implemented via network interface 740.

As shown in FIG. 6, memory 720 may include program instructions 725, configured to implement embodiments of the method 500 as described herein, and data storage 735, comprising various data accessible by program instructions 725.

Those skilled in the art will appreciate that computer system 700 is merely illustrative and is not intended to limit the scope of a calibration module or calibration method as described herein. In particular, the computer system and devices may include any combination of hardware or software that can perform the indicated functions. The computer system 700 may also be coupled to the ophthalmic apparatus 100 and any other devices that are not illustrated, or instead may operate as a stand-alone system. In addition, the functionality provided by the illustrated components may in some embodiments be combined in fewer components or distributed in additional components. Similarly, in some embodiments, the functionality of some of the illustrated components may not be provided and/or other additional functionality may be available.

In compliance with the statute, the invention has been described in language more or less specific to structural or methodical features. The term "comprises" and its variations, such as "comprising" and "comprised of" is used throughout in an inclusive sense and not to the exclusion of any additional features.

It is to be understood that the invention is not limited to specific features shown or described since the means herein described comprises preferred forms of putting the invention into effect.

The invention is, therefore, claimed in any of its forms or modifications within the proper scope of the appended claims appropriately interpreted by those skilled in the art.

Throughout the specification and claims (if present), unless the context requires otherwise, the term "substantially" or "about" will be understood to not be limited to the value for the range qualified by the terms.

Any embodiment of the invention is meant to be illustrative only and is not meant to be limiting to the invention. Therefore, it should be appreciated that various other changes and modifications can be made to any embodiment described without departing from the spirit and scope of the invention.

The invention claimed is:

1. A method of calibration for an ophthalmic plenoptic camera system to determine a true size of a feature of the retina of a subject's eye based on an acquired light-field image or light-field images of the retina, wherein the imager comprises: an illumination light source and an optical assembly for directing light from the light source into an eye of a subject; an objective lens positioned along an imaging axis intersecting a point on the fundus of the eye; a photosensor positioned for acquiring images of portions of a fundus of the eye and a microlens array positioned in between the objective lens and the photosensor such that each microlens in the array projects a different view of the image formed at the image plane thereby forming an array of elemental images on the photosensor; the method comprising:
acquiring an initial image of the retina;
extracting matching features from views derived from a plurality of elemental images forming the initial image;
calculating at least one functional relationship between two or more of said views having matching features so that the plenoptic camera system is calibrated on the basis of the calculated functional relationship.

2. A method in accordance with claim 1 wherein the calculating step comprises calculating at least two functional relationships between two or more said views having matching features.

3. A method in accordance with claim 1 further comprising the step of applying the functional relationship to calculate the true size of a feature in the retina of the subject's eye.

4. A method in accordance with claim 1 wherein the step of extracting matching features comprises applying a feature detecting step by identifying groups of two or more points that are easily distinguishable in the two or more views to produce a set of matching pairs.

5. A method in accordance with claim 4 wherein the step of producing matching pairs is followed by a co-matching step between the matching pairs across the corresponding views to obtain co-matches between match pairs and subsequently appending the co-matches together to obtain a cluster of matching points across the corresponding views.

* * * * *